(12) United States Patent
Heeg et al.

(10) Patent No.: US 7,943,182 B2
(45) Date of Patent: May 17, 2011

(54) BERRY OILS AND PRODUCTS

(76) Inventors: Timothy Heeg, Nekoosa, WI (US);
Bernard G. Lager, Wisconsin Rapids, WI (US)

( * ) Notice: Subject to any disclaimer, the term of this patent is extended or adjusted under 35 U.S.C. 154(b) by 776 days.

(21) Appl. No.: 11/568,662

(22) PCT Filed: May 3, 2005

(86) PCT No.: PCT/US2005/015175
§ 371 (c)(1),
(2), (4) Date: Dec. 26, 2007

(87) PCT Pub. No.: WO2005/107476
PCT Pub. Date: Nov. 17, 2005

(65) Prior Publication Data
US 2008/0199547 A1 Aug. 21, 2008

Related U.S. Application Data

(60) Provisional application No. 60/567,631, filed on May 3, 2004.

(51) Int. Cl.
*A61K 36/04* (2006.01)

(52) U.S. Cl. ......... 424/732; 426/615; 426/638; 426/648

(58) Field of Classification Search .................. None
See application file for complete search history.

(56) References Cited

U.S. PATENT DOCUMENTS

| | | | |
|---|---|---|---|
| 3,554,766 A * | 1/1971 | Engel et al. | 426/307 |
| 3,875,215 A | 4/1975 | Strycker | |
| 4,006,252 A | 2/1977 | Lerner | |
| 4,935,243 A * | 6/1990 | Borkan et al. | 424/441 |
| 5,767,152 A | 6/1998 | Nielsen et al. | |
| 5,798,345 A | 8/1998 | Knutson et al. | |
| 5,843,987 A | 12/1998 | Rajagopalan et al. | |
| 5,908,839 A | 6/1999 | Levitt et al. | |
| 6,231,866 B1 | 5/2001 | Mann | |
| 6,391,345 B1 | 5/2002 | Heeg et al. | |
| 6,641,847 B1 | 11/2003 | Nawar | |
| 6,646,144 B1 | 11/2003 | Klein et al. | |
| 6,733,798 B2 * | 5/2004 | Heeg et al. | 424/732 |
| 2002/0004749 A1 * | 1/2002 | Froseth et al. | 705/16 |
| 2002/0168429 A1 | 11/2002 | Mann | |
| 2003/0219501 A1 | 11/2003 | Day | |
| 2007/0281044 A1 | 12/2007 | Mueller et al. | |
| 2008/0107758 A1 | 5/2008 | Crutchfield | |

FOREIGN PATENT DOCUMENTS

| | | |
|---|---|---|
| JP | 2001097876 A2 | 4/2001 |
| JP | 2002241299 A2 | 8/2002 |
| JP | 2006153783 A2 | 6/2006 |
| RU | 1832026 | 8/1993 |
| SU | 1312089 | 5/1987 |
| SU | 1312089 A | 5/1987 |
| WO | WO-00/72862 | 12/2000 |

OTHER PUBLICATIONS

Stoner, G., "Berry Works News", *a grower newsletter for the Oregon Commission, Oregon Raspberry & Blackberry Commission, Oregon Strawberry Commission, Fall 2001 Edition*, (2001), pp. 1-11.

"International Search Report for Application No. PCT/SE 2005/015175, Date mailed May 3, 2005", 10 Pages.

"U.S. Appl. No. 10/794,860, Non-Final Office Action mailed Oct. 9, 2009", 13 pgs.

"U.S. Appl. No. 10/794,860, Response filed Aug. 19, 2009 to Advisory Action mailed Jun. 17, 2009", 7 pgs.

"U.S. Appl. No. 10/794,860, Response filed Apr. 21, 2010 to Non-Final Office Action mailed Oct. 9, 2009", 7 pgs.

"U.S. Appl. No. 10/794,860, Response filed Jun. 8, 2009 to Final Office Action mailed Apr. 6, 2009", 7 pgs.

"Japanese Application No. 2007-511470, Office Action mailed Nov. 17, 2009", 8 pgs.

Croteau, et al., "Seed lipids of the American Cranberry(Vaccinium macrocarpon)", *Phytochemistry*, 8(11), 2219-2222.

Maneatis, John G., "Low-Jitter Process-Independent DLL and PLL Based on Self-Biased Techniques", *IEEE Journal of Solid-State Circuits*, 31(11), (Nov. 1996), 1723-1732.

Parker, T. D, et al., "Fatty Acid Composition and Oxidative Stability of cold-pressed Edible Seed Oils.", *1240 Journal of Food Science—* vol. 68,(4), (2003).

"U.S. Appl. No. 10/794,860 Final Office Action mailed Jul. 26, 2010", 12 pgs.

\* cited by examiner

*Primary Examiner* — Christopher R. Tate
(74) *Attorney, Agent, or Firm* — Schwegman, Lundberg & Woessner, P.A.

(57) ABSTRACT

The invention includes embodiments of berry oils, cold pressed, and products incorporating the berry oils.

7 Claims, 1 Drawing Sheet

US 7,943,182 B2

BERRY OILS AND PRODUCTS

RELATED APPLICATION

This application is a nationalization under 35 U.S.C. 371 of PCT/US2005/015175, filed May 3, 2005 and published as WO 2005/107476 A2 on Nov. 17, 2005, which claimed priority from U.S. Provisional Application Ser. No. 60/567,631 filed May 3, 2004, and as a Continuation-In-Part of pending U.S. patent application Ser. No. 10/794,860 filed Mar. 5, 2004, which is a divisional of U.S. patent application Ser. No. 10/152,078 filed May 10, 2002, issuing into U.S. Pat. No. 6,733,798, which is a divisional of U.S. patent application Ser. No. 09/597,593 filed Jun. 16, 2000, issuing into U.S. Pat. No. 6,391,345, which claimed priority from U.S. Provisional Application Ser. No. 60/203,775 filed May 12, 2000.

TECHNICAL FIELD

Embodiments of the invention described herein are related to oils and flours obtained from a variety of berry types.

BACKGROUND

American cranberries, *Vaccinium macrocarpon*, are native plants of open, acid peat bogs in North America. Cranberry plants are evergreen perennial vines that produce runners and upright branches with terminal flower buds.

Cranberries have historically been harvested and either ingested as whole berries, such as in cranberry sauce, or have been processed for their juice. Pulp remaining after cranberry juice extraction processing has historically been regarded as an undesirable waste product with little or no utility.

In the United States, cranberries are grown and are harvested in the Northeast, Northwest and Great Lakes regions. Cranberries ripen and are harvested in Autumn, which has made cranberries a holiday food. Cranberries have not changed significantly in appearance and nutritional value over time. Cranberries have typically been stored by freezing or drying the whole berries.

Cranberries have become a popular food only in recent years because cranberries have a very bitter taste. Historically, processors have not dealt well with the taste. Cranberries are known to contain quininic acid. It is the quininic acid that imparts to cranberries, the bitter taste. Cranberry juice has become more palatable because it is blended with other sugar-containing aqueous liquids.

Apart from an undesirable taste, quininic acid is believed to have nutraceutical properties. When ingested, quininic acid is converted to hippuric acid. Hippuric acid is believed to remove toxins from the bladder, kidneys, prostate and testicles.

SUMMARY

One embodiment includes a nutraceutical comprising one or more of cranberry seed oil, cranberry flour, and freeze dried whole cranberries. Another embodiment includes a nutraceutical comprising cranberry seed oil. Other embodiments include a capsule comprising cranberry flour; a capsule comprising ellagic acid; a nutraceutical comprising red raspberry flour; and a topical formulation comprising red raspberry oil or flour or both. Another embodiment includes a nutraceutical comprising red raspberry oil. Other embodiments include an antioxidant comprising cranberry flour and a method for protecting skin from damage produced by UV radiation comprising application of a formulation comprising ellagic acid. Another embodiment includes a nutraceutical comprising dried cranberry particles, cranberry seed oil and omega-3 fatty acids.

Other embodiments include an evergreen blackberry oil produced by cold extrusion and filtration at a temperature not exceeding 100° C.; nutraceutical comprising evergreen blackberry oil; and one or more of a nutrition bar, powder, dietary supplement, pet food, nutraceutical, dietary or topical formulation comprising black raspberry seed extract.

Other embodiments include a dietary fiber comprising black raspberry seeds; one or more of a nutrition bar, powder, dietary supplement, pet food, nutraceutical, dietary or topical formulation comprising evergreen blackberry seed extract; a blend comprising cranberry oil and olive oil; a topical application comprising cranberry oil and olive oil; and a formulation comprising ellagic acid extract in a concentration of at least about 550 ppm.

Additional embodiments include a carrier comprising one or more of cranberry seed oil, evergreen blackberry seed oil, black raspberry seed oil, olive oil, and red raspberry seed oil; a delivery system comprising one or more of cranberry seed oil, evergreen blackberry seed oil, black raspberry seed oil, olive oil, and red raspberry seed oil.

DESCRIPTION

Figure 1:
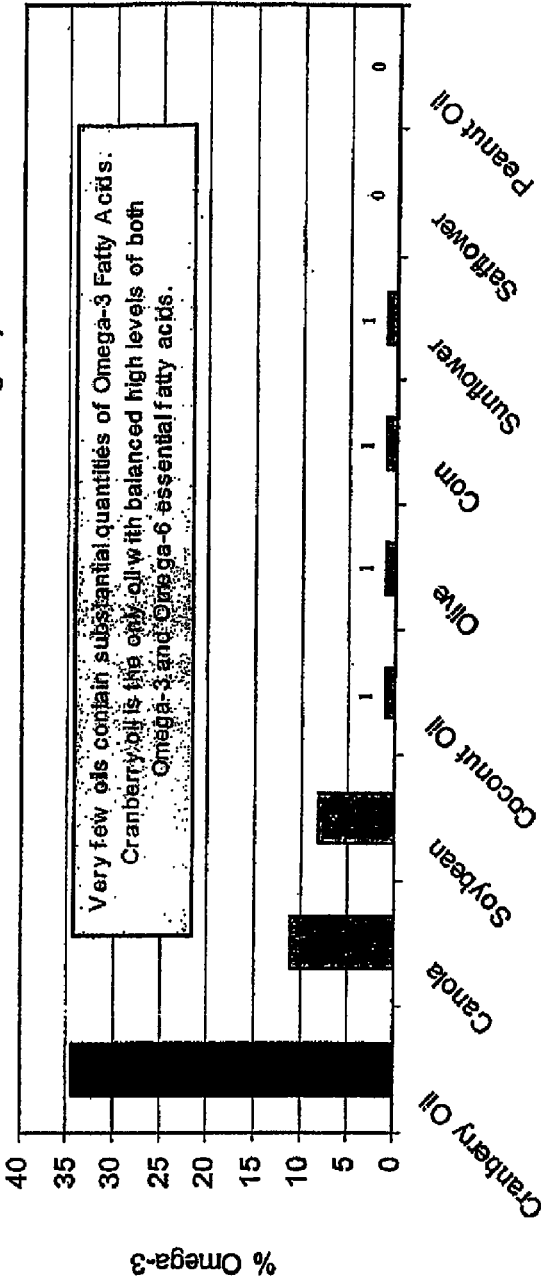
FIG. 1 is a graphical view of Omega-3 fatty acids in plant oils.

In the following detailed description of exemplary embodiments of the invention, reference is made to the accompanying drawings (where like numbers represent like elements), which form a part hereof, and in which is shown, by way of illustration, specific exemplary embodiments in which the invention may be practiced. These embodiments are described in sufficient detail to enable those skilled in the art to practice the invention. It is to be understood that other embodiments may be utilized and logical, mechanical, electrical or other changes may be made without departing from the scope of the inventive subject matter described herein.

Embodiments of the invention described herein include a nutraceutical that includes cranberry seed oil, cranberry flour, and freeze dried whole cranberries; a capsule comprising cranberry flour; and a capsule comprising ellagic acid; a nutraceutical that includes red raspberry flour; a topical formulation comprising red raspberry oil or flour or both; a nutraceutical comprising red raspberry oil; a method for maintaining urinary tract health; an evergreen blackberry oil produced by cold extrusion and filtration at a temperature not exceeding 100° C.; a blend comprising cranberry oil and olive oil; a dietary fiber comprising black raspberry seeds; a carrier comprising one or more of cranberry seed oil, evergreen blackberry seed oil, black raspberry seed oil, olive oil, and red raspberry seed oil; and a delivery system comprising one or more of cranberry seed oil, evergreen blackberry seed oil, black raspberry seed oil, olive oil, and red raspberry seed oil.

Products described herein are free of enzymes, extraction solvents, oxygen and are not formulated with synthetic processes.

Cold press process embodiments employed for extraction of berry seed flour and oil are described in U.S. Pat. No. 6,391,345, which is incorporated by reference. The cold press process extracts oils without use of enzymes, extraction solvents, or synthetic processes.

Invention embodiments are described in the categories following herein.

Cranberry

One cranberry formulation embodiment is a nutraceutical formulation that is a blend of cranberry solids, protein and lipids and gelatin. The formulation is delivered in soft gel capsules stored in a labeled bottle with a tamper evident seal and cotton stuffing. Each capsule includes 500 mg of cranberry flour, 400 mg of freeze dried whole cranberries, 100 mg of cranberry lipid extract and 17.5 mg of total phenolics. This formulation has use in treating symptoms associated with urinary tract health, without requiring the user to ingest additional calories associated with cranberry juice. The formulation provides protein, antioxidant phenolics and balanced concentrations of omega-3 and omega-6 essential fatty acids (EFA). It is believed that fruit fiber, including cranberry fiber has use in reducing blood cholesterol, cardiovascular disease and diabetes.

Another cranberry nutraceutical formulation embodiment includes cranberry seed oil in soft gel capsules. Each capsule includes a fatty acid composition of alpha-linolenic acid (omega-3) of 351 mg; linoleic acid (omega-6) in a concentration of 342 mg; oleic acid (omega-9) in a concentration of 281 mg; tocopherols and tocotrienols of 5587 mcg and phytosterols as beta-sitosterol of 1000 mcg.

Another cranberry nutraceutical formulation includes cranberry protein capsules. The formulation is dispensed in soft gel capsules. Each capsule includes cranberry flour having the following formulation: phenolics—11.05 mg; protein—250 mg; aspartic acid—2.33 g/100 g; isoleucine—0.78 g/100 g; threonine—0.65 g/100 g; luecine—1.73 g/100 g; serine—0.92 g/100 g; tyrosine—0.63 g/100 g; glutamic acid—5.59 g/100 g; phenylalanine—1.07 g/100 g; praline—0.91 g/100 g; histidine—0.55 g/100 g; glycine—1.41 g/100 g; lysine—0.74 g/100 g; alanine—1.16 g/100 g; arginine—2.91 g/100 g; valine—1.11 g/100 g; cysteine (after oxidation)—0.46 g/100 g; methionine—0.24 g/100 g and methionine (after oxidation)—0.64 g/100 g.

The soft gel capsule formulations containing cranberry flour and oil protect the omega-3 with naturally occurring antioxidants, phytosterols and phospholipids. The soft gels do not have a grassy or fishy aftertaste that is associated with flax and fish oils.

Cranberry seed flour is a complete protein source, including all nine essential amino acids. The cranberry seed flour has a high mineral content of potassium in a concentration of 5684 ppm and calcium of 1461 ppm. The cranberry seed flour has a high fiber content of 50% dietary fiber and 46% insoluble fiber. The cranberry seed flour has an essential lipid concentration of 4%.

The cranberry seed flour is mildly abrasive, supports a natural desquamation process, has a red visual appeal and has use in scrubs, cleansers, soaps, and spa products.

The cranberry capsules containing cranberry protein have been shown to have an antioxidant potency that is about eight-times more powerful than beta-carotene and four times more powerful than Vitamin E. Cranberry protein is unique in that it is the only 100 percent plant protein that contains 25% complete protein, including all branched chain amino acids (BCAA). Thus, the cranberry protein is a useful supplement to the diets of vegans, vegetarians, and other health conscious consumers. Additionally, cranberry protein is high in dietary fiber, antioxidant phenolics and minerals, such as potassium.

Another cranberry formulation includes 85% cranberry protein powder blended with 15% cranberry seed oil. The protein powder and cranberry seed oil are products of the cold press process described above. The formulation has proximates that include a moisture of about 4.7 gms; protein of about 22.8 gms; fat of about 15.0 gms; ash of 2.3 gms; and carbohydrates of about 55.2 gms. The formulation includes fiber having total dietary fiber of 45.4 gms; soluble fiber of 4.7 gms; and insoluble fiber of 40.7 gms. The formulation additionally includes minerals of potassium of 504 mg; calcium of 129.7 mg; sodium of 11.98 mg and iron of 3.02 mg. The formulation additionally includes fat having saturated fat of 1.03 gms; polyunsaturated fat of 10.4 gms; mono-unsaturated fat of 3.53 gms and trans fatty acids of 0.02 gms.

Another embodiment includes a mixture of freeze dried cranberries coated with cranberry flour and cranberry oil. This mixture is a rich source of fiber as well as ingredients of cranberry oil and cranberry flour. While cranberry is described, it is believed that cranberry oil and flour is usable to coat other fruits or vegetables. Also, while cranberry flour and cranberry oil are described, it is believed that other berry flours and oils are suitable for use with other fruits and vegetables.

In one embodiment, a bread product was made that included cranberry flour. The bread contained tocopherols, tocotrienols, phytoseterols and lecithin. While bread is described, it is believed that cranberry flour has uses in other food products.

A fatty acid profile for this product is as follows:

| Fatty Acid Profile: | |
|---|---|
| Linoleic: | 3478 mg |
| Alpha-linolenic: | 3375 mg |
| Oleic: | 2289 mg |
| Palmitic: | 539 mg |
| Stearic: | 108 mg |
| 11-Transeicosenoic: | 22 mg |
| Gamma-linolenic: | 17 mg |
| Palmitoleic: | 13 mg |
| Nonadecanoic: | 12 mg |
| 11-14 Eicosandienoic: | 10 mg |
| Other: | 38 mg |

| Amino Acids: | | | |
|---|---|---|---|
| Aspartic Acid: | 2.08 g | Isoleucine: | 0.69 g |
| Threonine: | 0.58 g | Leucine: | 1.54 g |
| Serine: | 0.82 g | Tyrosine: | 0.57 g |
| Glutamic Acid: | 4.99 g | Phenylalanine: | 0.96 g |
| Proline: | 0.81 g | Histidine: | 0.49 g |
| Glycine: | 1.26 g | Lysine: | 0.66 g |
| Alanine: | 1.05 g | Arginine: | 2.59 g |
| Valine: | 0.99 g | Cysteine (after oxidation): | 0.41 g |
| Methionine: | 0.29 g | Methionine (after oxidation): | 0.57 g |
| | | Tryptophan (after hydrolosis): | 0.28 g |

| Antioxidants: | |
|---|---|
| Alpha-tocopherol: | 364 mcg/g |
| Alpha-tocotrienol: | 14 mcg/g |
| Beta-tocopherol: | 89 mcg/g |
| Gamma-tocopherol: | 11 mcg/g |
| Gamma-tocotrienol: | 168 mcg/g |
| Phynolics: | 6 mg/g |
| Anthocyanins: | 0.8 mg/g |

| Phytosterols: | |
|---|---|
| Campesterol: | 1.0 mg |
| Stigmasterol: | 1.1 mg |
| Beta-Sitosterol: | 13.0 mg |

One other cranberry formulation includes 90% cranberry protein powder blended with 10% cranberry seed oil. This formulation has the following analysis:

| Fatty Acid Profile: | |
|---|---|
| Linoleic: | 5269 mg |
| Alpha-linolenic: | 5113 mg |
| Oleic: | 3468 mg |
| Palmitic: | 816 mg |
| Stearic: | 163 mg |
| 11-Transeicosenoic: | 33 mg |

-continued

| | | |
|---|---|---|
| Gamma-linolenic: | | 25 mg |
| Palmitoleic: | | 20 mg |
| Nonadecanoic: | | 18 mg |
| 11-14 Eicosandienoic: | | 15 mg |
| Other: | | 58 mg |

Amino Acids:

| | | | |
|---|---|---|---|
| Aspartic Acid: | 1.98 g | Isoleucine: | 0.66 g |
| Threonine: | 0.55 g | Leucine: | 1.47 g |
| Serine: | 0.78 g | Tyrosine: | 0.54 g |
| Glutamic Acid: | 4.75 g | Phenylalanine: | 0.91 g |
| Proline: | 0.77 g | Histidine: | 0.47 g |
| Glycine: | 1.20 g | Lysine: | 0.63 g |
| Alanine: | 0.99 g | Arginine: | 2.47 g |
| Valine: | 0.94 g | Cysteine (after oxidation): | 0.39 g |
| Methionine: | 0.28 g | Methionine (after oxidation): | 0.54 g |
| | | Tryptophan (after hydrolosis): | 0.27 g |

Antioxidants:

| | |
|---|---|
| Alpha-tocopherol: | 551 mcg/g |
| Alpha-tocotrienol: | 21 mcg/g |
| Beta-tocopherol: | 135 mcg/g |
| Gamma-tocopherol: | 17 mcg/g |
| Gamma-tocotrienol: | 255 mcg/g |
| Phynolics: | 9 mg/g |
| Anthocyanins: | 1.3 mg/g |

Phytosterols:

| | |
|---|---|
| Campesterol: | 1.0 mg |
| Stigmasterol: | 1.1 mg |
| Beta-Sitosterol: | 19.8 mg |

Beta-sitosterol has been found to have possible activity in promoting prostate health and in reducing cholesterol. It is believed that the L-arginine may have use in inhibiting cardiovascular disease, treating some forms of male infertility, treating some kidney disorders, and accelerating wound healing. L-arginine may also have a role in treating erectile dysfunction, migraine, liver disease and primary ciliary dyskinesia. Branched chain amino acids may have some antihepatic encephalopathy activity and antitardive dyskinesia activity. The tocotrienols may have greater hypolipidemic effects than the tocopherols. The phytostanols may have use in managing hypercholesterolemia. The phytosterols have use in lowering cholesterol.

Cranberry 90/10

Cranberry 90/10 is 90% Cranberry Protein Powder blended with 10% Cranberry Seed Oil. Cranberry 90/10 is produced by a cold extrusion and filtration process from the seeds described in U.S. Pat. No. 6,391,345, which is incorporated by reference, of the American cranberry (*Vaccinium macrocarpon Ait.*) without enzymes or extraction solvents. The powder is a concentrated source of complete protein, essential amino acids, branched chain amino acids, ultra-stable omega-3 EFA and phytosterols.

| Identification: | |
|---|---|
| Botanical Family: | *Vaccinium Macrocarpon* Ait. 100% |
| Characteristics: | |
| Appearance: | Reddish-brown powder |
| Odor: | Characteristic of grain flour with mild cranberry aroma |
| Shelf Life: | 24 months from manufacture date |

-continued

| Typical Analysis (per 100 g): | |
|---|---|
| Proximates: | |
| Moisture: | 4.9 g |
| Protein: | 23.2 g |
| Fat: | 10.0 g |
| Ash: | 2.4 g |
| Carbohydrates: | 58.2 g |
| Fiber: | |
| Total Dietary Fiber: | 45.9 g |
| Soluble Fiber: | 4.6 g |
| Insoluble Fiber: | 41.3 g |
| Minerals: | |
| Potassium: | 426 mg |
| Calcium: | 129.7 mg |
| Sodium: | 83.1 mg |
| Iron: | 3.70 mg |
| Fat: | |
| Saturated Fat: | .07 g |
| Polyunsaturated Fat: | 6.9 g |
| Monounsaturated Fat: | 2.3 g |
| Trans Fatty Acids: | 0.02 g |

Another embodiment includes cranberry pieces fortified with omega-3. These pieces are 100% cranberries—sweet and dried cranberry pieces. The pieces are coated or sprayed with 3% cranberry seed oil and 1% omega-3 essential fatty acids. The cranberry pieces have application in bars, chews, trail mixes, functional foods and conventional foods. The cranberry seed oil is added to the sweet and dried cranberry pieces to provide nutritional omega-3 essential fatty acids, antioxidants and phytosterols. The cranberry pieces are dark red fruit pieces having a piece size of about ⅛ inch. The product includes sweet and dry cranberry pieces in a concentration of 97%, cranberry seed oil of 3.0% and linolenic acid (18:3) of 1.0%.

One additional product embodiment is a blend of olive oil and cranberry oil. The berry seed oils described herein have also been found to act as carriers and delivery systems.

The cranberry seed oil formulations have unique fatty acid profiles, superior antioxidant profiles, and superior phytochemical profiles. In particular, the fatty acid profile includes 70% total PUFA, 35% linoleic acid (omega-6), 35% alpha-linolenic acid (omega-3), 23% oleic acid, and 5% palmitic acid. The cranberry seed oil has a 1:1 ratio of omega-3:omega-6 fatty acids. A comparison of omega-3 fatty acid is compared to other material in FIG. 1.

The antioxidant profile for the cranberry seed oil includes alpha-tocopherol of 341 mg/kg; gamma-tocopherol of 111 mg/kg and gamma-tocotrienol of 1700 mg/kg. The cranberry seed oil has the highest tocotrienol concentration of all edible oils.

The phytochemical profile includes phytosterols of campesterol/brassicasterol of 66 mg/kg; stigmasterol of 68 mg/kg; beta-sitosterol of 1319 mg/kg and phospholipids of phosphatidylinositoil of 9.9 mg/kg, and phosphatidylcholine of 202 mg/kg.

The cranberry seed oil extract includes a concentrated source of potent antioxidant phenolics and anthocyanin with phenolics in a concentration of 11.05 mg/g and anthocyanin of 1.52 mg/g. The seed extract is free from a carrier or added agents.

When used as an antioxidant, the cranberry seed extract supports formulation integrity and skin defense systems.

The cranberry seed extract is mildly abrasive and has use in oral care applications. The cranberry seed extract physically removes dental plaque from teeth, gums and tongue. The cranberry seed extract is anti-adhesive and inhibits bacteria adhesion. This application is unique to the cranberry seed extract because cranberry juice is typically formulated with high dextrose and fructose concentrations and is unsuitable for promoting oral hygiene.

Red Raspberry Flour

Ellagic acid, extracted from Meeker red raspberries has been found to have antioxidant, antibacterial, antimutagenic, anticarcinogenic, antiviral and hepatoprotectant properties. It is believed that ellagic acid extract provides protection against chromosomal damage produced by UV radiation and promotes aopototic growth of cervical cancer cells. The ellagic acid also was observed to have similar effects on breast, pancreas, esophageal, skin, colon, leukemia and prostate cancer cells. The ellagic acid is also believed to promote wound healing. Ellagic acid has been found t exhibit anticarcinogenic and antimutagenic activity and functions as an endogenous and exogenous antioxidant. The ellagic acid inhibits tumor growth and protects against chromosome damage and strand breaks from radiation therapy. Ellagic acid concentrations extracted from Meeker red raspberries includes about 550 ppm ellagic acid.

Ellagic acid is an organic phenolic compound naturally biosynthesized in plants. Ellagic acid is a result of biodegradation of ellagitannins, which are hydrolysable tannins. Ellagitannins are esters of glucose with hexahydroxydiphenic acid (HHDP) that when hydrolyzed, yield ellagic acid. Technically, polymers of gallic acid and HHDP link to glucose to form ellagitannins. When two gallic acid groups become linked side by side within a tannin molecule, the HHDP group is formed. Ellagic acid results when HHDP is cleaved from a tannin molecule and is spontaneously rearranged.

Raspberry flour is a source of ellagic acid. One formulation of an ellagic acid extract includes soft gel capsules of red raspberry flour of 1000 mg; phenolics of 41.17 mcg; ellagic acid of 450 ppm and soluble fiber of 50 mg.

The raspberry flour is manufactured using the cold press process described above.

Red Raspberry Seed Oil

Meeker red raspberry seed oil includes 85% essential fatty acids (EFA) and has an excellent antioxidant profile, a high saponification value and UV absorbance capacity. The seed oil has about 85% essential fatty acids that include 55% omega-6 linoleic acid and 35% omega-3 linolenic acid and 12% omega-9 oleic acid.

Topical application of EFAs provide a lipid barrier protection, moisture retention, TEWL reduction, rapid penetration and anti-inflammatory.

The antioxidant profile includes alpha tocopherol of 144 mg/g; gamma tocopherol of 144 mg/g and mixed carotenoids of 3 mg/100 g.

The Meeker red raspberry seed oil has a saponification value of 187 to 192, which is excellent for soap production and as a superfatting agent.

The Meeker red raspberry seed oil has a UVC of 100-290 nm, a UVB of 290 to 320 nm and a UVA of 320 to 400.

The cranberry seed oil and red raspberry seed oil act as emollients, lubricants, skin conditioning agents. The oils have high stability antioxidant oil, and act as excellent carrier oils. The oils have activity as semi-occlusive agents, and superfatting agents. The oils have high saponification values, UV photoprotection, and act as a vegetable oil alternative.

Black Raspberry Seed Extract

Black raspberry seed extract is cold-press extruded from the seeds of Black Raspberry (*Rubus Occidentalis*) without enzymes or solvents. Black raspberry seed extract contains no carrier or added agents and is ideal for applications such as nutrition bars, powder products, dietary supplements, pet foods, medical foods and dietary and topical applications. The black raspberry seed extract has high concentrations of soluble fiber with a mild raspberry flavor and aroma. The black raspberry seed extract has the following formulation:

Black Raspberry Seed Extract is cold-press extruded from the seeds of Black Raspberry (*Rubus Occidentalis*) without oxygen, enzymes or solvents. Black Raspberry contains no carrier or added agents and is ideal for various proactive and protective nutritional applications. Features of the black raspberry seed extract are as follows:

| Identification: | |
| --- | --- |
| Botanical Name: | *Rubus Occidentalis* |
| Characteristics: | |
| Appearance: | Purple powder |
| Odor: | Characteristic of grain flour with slight raspberry aroma |
| Particle Size: | 100% through 80 mesh (0.020") screen |
| Other Ingredients: | none |
| Shelf Life: | 24 months from manufacture date |
| Typical Analysis: | |
| Moisture: | 6.8% |
| Protein: | 13.1% |
| Fat: | 7.8% |
| Ash: | 2.08% |
| Soluble Fiber: | 6.8% |
| Insoluble Fiber: | 43.6% |
| Microbiological Tests: | |
| Aerobic Plate Count: | 30 cfu/g |
| *E. coli*: | n.d. cfu/g |
| Total Coliform: | n.d. cfu/g |
| *Staphylococcus aureus*: | n.d. cfu/g |
| *Salmonella*: | negative org/25 g |
| Yeast & Mold: | n.d. cfu/g |

Description:

This product is produced by patented cold-press extrusion from the seeds of *Rubus Occidentalis* var. *strigosus* (Black Raspberry) without oxygen, enzymes or solvents at temperatures not exceeding 100° F.

Physical Characteristics:

There might be slight differences in physical characteristics due to natural variation in raw material.

| Appearance: | Bright gold oil |
| --- | --- |
| Odor: | Characteristic of vegetable oil, mild raspberry aroma |
| Specific Gravity: | 0.928 |
| Shelf Life: | 24 months from manufacture date |
| Additives: | None |

Evergreen Blackberry Seed Oil

Evergreen blackberry seed oil is pressed in a process such as the cold press process described above. The evergreen blackberry seed oil has the following components:

Evergreen Blackberry Seed Oil is produced by a proprietary cold extrusion and filtration process from the seeds of the Evergreen Blackberry (*Rubus Laciniatus*) without enzymes or extraction solvents at temperatures not exceeding 100° F. Exceptionally stable, this highly unsaturated triglyceride oil possesses naturally occurring fatty acid, antioxidant and phytosterol profiles.

| Identification: | |
|---|---|
| Botanical Family: | *Rubus Laciniatus* |
| Characteristics: | |
| Appearance: | Dark green oil |
| Odor: | Characteristic of vegetable oil, mild fruity aroma |
| p11 as supplied: | 4.2-5.2 |
| Specific Gravity: | 0.910-.930 |
| Shelf Life: | 24 months from manufacture date in sealed unopened original containers. Opened containers should be packaged under nitrogen. Material kept beyond shelf life is not necessarily unusable, but a quality control should be performed on the properties relevant to the application. |
| Typical Analysis: | |
| Peroxide Value: | 1-16.0 meq/kg |
| Unsaponifiables: | <2.0% |
| Free Fatty Acids: | <1.0% |
| Saturated Fat: | <4.0% |
| Oleic Acid (18:1): | <21.0% |
| Polyunsaturated Fat: | >68.0% |
| Linoleic Acid (18:2): | >50.0% |
| Linolenic Acid (18:3): | >18.0% |
| Stigmasterol: | >500 mcg/g |
| Campesterol: | >350 mcg/g |
| Beta-Sitosterol: | >5500 mcg/g |
| Alpha-tocopherol: | >1800 mcg/g |
| Alpha-tocotrienol: | >110 mcg/g |
| Beta-tocopherol: | >400 mcg/g |
| Gamma tocopherol: | >100 mg/g |
| Lutein: | >11 mcg/g |

Evergreen Blackberry Seed Extract

The evergreen blackberry seed extract is cold-pressed extruded without enzymes, solvents or oxygen from evergreen blackberry seeds. The powdered extract has a high concentration of soluble fiber with a mild fruity aroma. The evergreen blackberry seed extract has application in nutrition bars, powder products, dietary products, pet foods, medical foods and dietary and topical applications. The evergreen blackberry seed extract has properties that include antioxidant, dietary fiber, blueberry taste and aroma and no carrier agents. The evergreen blackberry seed extract has the following features:

Evergreen Blackberry Seed Extract is cold-press extruded from the seeds of the Evergreen Blackberry (*Rubus Lacinatus*) without oxygen, enzymes or solvents. Evergreen Blackberry contains no carrier or added agents and is ideal for various proactive and protective nutritional applications.

| Identification: | |
|---|---|
| Botanical Name: | *Rubus Occidentalis* |
| Characteristics: | |
| Appearance: | Bright Tan powder |
| Odor: | Characteristic of grain flour with slight taste of blackberry |
| Particle Size: | 100% through 80 mesh (0.020") screen |
| Other Ingredients: | none |
| Shelf Life: | 24 months from manufacture date |
| Typical Analysis: | |
| Moisture: | 2.3% |
| Protein: | 10.2% |
| Fat: | 6.2% |
| Ash: | 1.62% |
| Soluble Fiber: | 3.8% |
| Insoluble Fiber: | 48.7% |
| Microbiological Tests: | |
| Aerobic Plate Count: | 170 cfu/g |
| *E. coli*: | n.d. cfu/g |
| Total Coliform: | n.d. cfu/g |
| *Staphylococcus aureus*: | n.d. cfu/g |
| *Salmonella*: | negative org/25 g |
| Yeast & Mold: | n.d. cfu/g |

Other Fruit Oil and Flour Products

Other fruit oils and flours and protein produced by a cold press process include gooseberry, blueberry, and elderberry, strawberry, and Saskatoon berry.

While specific products are described, it is understood that other products may be produced by the products described herein. The products include peanut butter with one or more of the fruit oils described herein, mayonnaise with one or more of the fruit oils described herein, vinaigrette, liquid soaps, antibacterial liquid soap, hair care products, exfoliants, skin care formulations, cosmetics, as a component in food products such as but not limited to oatmeal and cereal, foot balm, lotions. Fruit oils, flours, protein and other products described herein may be blended with cooking oil such as but not limited to soy, canola, vegetable, palm, safflower, and sunflower. Berry fiber products are also believed to have use as colon cleansers.

While specific oil flour concentration ratios are described herein, it is understood that other ratios are also suitable for use.

It will be readily understood to those skilled in the art that various other changes in the details, material, and arrangements of the parts and method stages which have been described and illustrated in order to explain the nature of this inventive subject matter may be made without departing from the principles and scope of the inventive subject matter as expressed in the subjoined claims.

What is claimed is:

1. A nutraceutical comprising a combination of cranberry seed oil, cranberry flour, and freeze dried whole cranberries wherein the cranberry seed oil and cranberry flour coat one or more of the freeze dried whole cranberries.

2. A food comprising the nutraceutical of claim 1.

3. The nutraceutical of claim 1 packaged as a soft gel.

4. The nutraceutical of claim 1, further comprising omega-3 linolenic acid in a concentration of 35.1% by weight, omega-6 linoleic acid in a concentration of 34.2% by weight, omega-9 oleic acid in a concentration of 28.1% by weight, tocopherols, tocotrienols and beta-sitosterol.

5. The nutraceutical of claim 1 comprising cranberry seed oil and cranberry flour wherein the ratio of cranberry flour to cranberry seed oil is 85:15.

6. The nutraceutical of claim 1 comprising cranberry seed oil and cranberry flour wherein the ratio of cranberry flour to cranberry seed oil is 90:10.

7. One or more of a bar, chew, trail mix, functional food or conventional food comprising the nutraceutical of claim 1.

* * * * *